US009168021B2

(12) United States Patent
Pernot et al.

(10) Patent No.: US 9,168,021 B2
(45) Date of Patent: Oct. 27, 2015

(54) METHOD AND APPARATUS FOR MEASURING HEART CONTRACTILITY

(75) Inventors: Mathieu Pernot, Paris (FR); Mickaël Tanter, Bagneux (FR); Mathieu Couade, Aix en Provence (FR); Mathias Fink, Meudon (FR)

(73) Assignees: Super Sonic Imagine, Aix En Provence Cedex (FR); CENTRE NATIONAL DE LA RECHERCHE SCIENTIFIQUE—CNRS, Paris Cedex (FR)

( * ) Notice: Subject to any disclaimer, the term of this patent is extended or adjusted under 35 U.S.C. 154(b) by 619 days.

(21) Appl. No.: 12/478,514

(22) Filed: Jun. 4, 2009

(65) Prior Publication Data
US 2010/0312116 A1 Dec. 9, 2010

(51) Int. Cl.
A61B 8/00 (2006.01)
A61B 8/08 (2006.01)
G01N 29/11 (2006.01)
G01S 7/52 (2006.01)

(52) U.S. Cl.
CPC .................. A61B 8/08 (2013.01); A61B 8/0883 (2013.01); A61B 8/485 (2013.01); G01N 29/11 (2013.01); G01S 7/52036 (2013.01); G01S 7/52042 (2013.01); G01N 2291/02827 (2013.01); G01N 2291/044 (2013.01); G01N 2291/0422 (2013.01)

(58) Field of Classification Search
CPC ........ A61B 8/08; A61B 8/0883; A61B 8/485; G01N 29/11; G01N 2291/0422; G01N 2291/044; G01N 2291/02827; G01S 7/52042; G01S 7/52036

USPC ......................................................... 600/453
See application file for complete search history.

(56) References Cited

U.S. PATENT DOCUMENTS

| 5,810,731 | A | 9/1998 | Sarvazyan et al. |
| 6,770,033 | B1 | 8/2004 | Fink et al. |
| 7,252,004 | B2 | 8/2007 | Fink et al. |
| 7,444,875 | B1 | 11/2008 | Wu et al. |
| 2005/0252295 | A1 | 11/2005 | Fink et al. |

(Continued)

FOREIGN PATENT DOCUMENTS

| WO | WO9819594 | 5/1998 |
| WO | WO-2004/021038 A1 | 3/2004 |

(Continued)

OTHER PUBLICATIONS

Kanai, Visualization of Propagation of Pulse Vibration along the Heart Wall and Imaging of its Propagation Speed, 2006, Proceedings of the 28th IEEE EMBS Annual International Conference, New York City, USA, 699-702.*

(Continued)

Primary Examiner — Bo J Peng
(74) Attorney, Agent, or Firm — Miller, Matthias & Hull LLP

(57) ABSTRACT

A Method for measuring heart contractility of a patient, in which a mechanical shear wave is propagated through the heart and observation of the propagation leads to determine a shear wave propagation parameter representative of the elasticity of the heart is disclosed. The value of the propagation parameter at the end of a systole is sampled, which leads to a parameter representative of the end systolic elastance.

15 Claims, 1 Drawing Sheet

(56) References Cited

U.S. PATENT DOCUMENTS

| | | |
|---|---|---|
| 2007/0049824 A1 | 3/2007 | Konofagou et al. |
| 2009/0112088 A1 | 4/2009 | Ohuchi et al. |

FOREIGN PATENT DOCUMENTS

| | | |
|---|---|---|
| WO | WO-2007/110375 A1 | 10/2007 |
| WO | WO-2008/135588 A2 | 11/2008 |
| WO | WO2008144490 | 11/2008 |

OTHER PUBLICATIONS

McLaughlin et al., Shear wave speed recovery in transient elastography and supersonic imaging using propagating fronts, 2006, Inverse Problems, 22, 681-706.*

Kanai et al., Myocardial Rapid Velocity Distribution, 2001, Ultrasound in Med. & Biol., vol. 27, No. 4, pp. 481-498.*

Sandrin et al., Shear Elasticity Probe for Soft Tissues with 1-D Transient Elastography, 2002, IEEE transactions on ultrasonics, ferroelectrics, and frequency control, vol. 49, No. 4, 436-446.*

Selzer et al., Improved common carotid elasticity and intima-media thickness measurements from computer analysis of sequential ultrasound frames, 2001, Atherosclerosis,154, 185-193.*

Online CME Breast Elastography, https://iame.com/online/breast_elastography/content.php , 2007.*

Bombardini, Myocardial contractility in the echo lab: molecular, cellular and pathophysiological basis, Cardiovascular Ultrasound, 2005, 3:27.*

Suga et al., Load Independence of the Instantaneous Pressure-Volume Ratio of the Canine Left Ventricle and Effects of Epinephrine and Heart Rate on the Ratio, Circ Res. 1973;32:314-322.*

Sagawa, et al., End-Systolic Pressure/Volume Ratio: A New Index of Ventricular Contractility; The American Journal of Cardiology vol. 40; 746-753 (1977).

Suga, et al., Load Independence of the Instantaneous Pressure-Volume Ratio of the Canine Left Ventricle and Effects of Epinephrine and Heart Rate on the Ratio; 314-322 (1973).

Chen-Huan, et al., Noninvasive Single-Beat Determination of Left Ventricular End-Systolic Elastance in Humans, JACC vol. 38, No. 7, 2001; Dec. 2001: 2028-34.

Kass, et al., From 'Ema' to pressure-volume relations: a broader view; Circulation 1988; 77; 1203-1212.

Sunagawa, et al., Effect of regional ischemia on the left ventricular end-systolic pressure-volume replationship of isolated canine hearts, Circulation Research (1983).

International Search Report from related PCT application No. PCT/EP2010/056128; report dated Jul. 20, 2010.

* cited by examiner

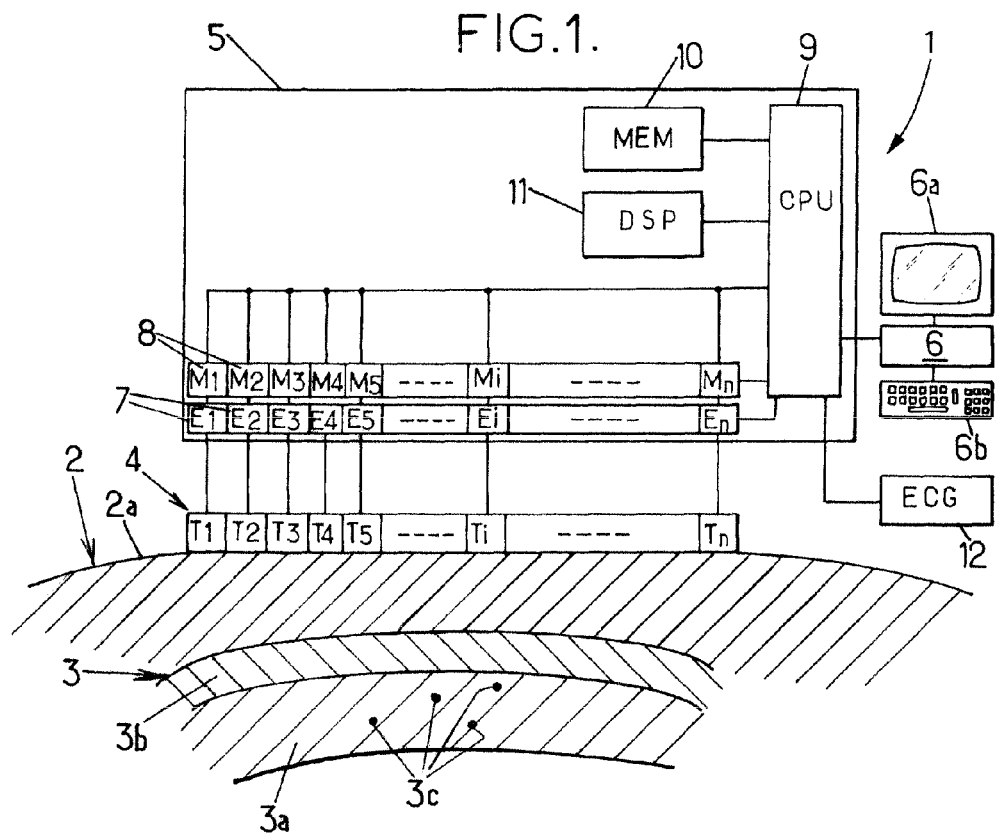
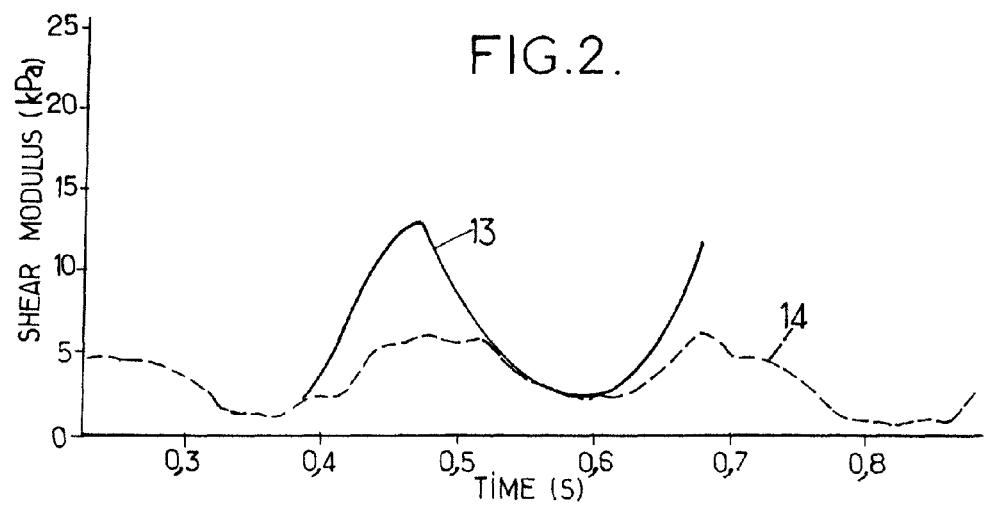

METHOD AND APPARATUS FOR MEASURING HEART CONTRACTILITY

FIELD OF THE DISCLOSURE

The invention relates to methods and apparatuses for measuring heart contractility.

BACKGROUND OF THE DISCLOSURE

Clinical evaluation of heart contractility is a crucial stake in cardiology, for detecting a number of cardiac pathologies such as dilated or hypertrophic cardiomyopathy, myocardial infarction, ischemia, etc.

Heart contractility is usually evaluated by assessing the End-Systolic Pressure-Volume Relationship (ESPVR), which normally requires a large number of invasive measurements on the patient, during several cardiac cycles. The ESPVR is a linear relation which is characterized in particular by its slope, the end-systolic elastance ($E_{max}$ or $E_{es}$).

Non-invasive methods to assess ESPVR have been designed to avoid this drawback. For instance, WO-A-98/19594 describes such a non-invasive, single beat measurement method, wherein measurements of pressure, heart volume and heart beat are carried out (some of them such as pressure estimation being even invasive), which are then used to estimate the ESPVR based on statistic data.

However, this known method is still complex since it requires simultaneous use of a lot of measurement devices. Further, this method is based on several assumptions:
  that the heart under examination follows the statistic laws used by the method,
  that elastance is a linear function of time,
  and that the volume-axis intercept of the Pressure-Volume diagram remains constant during a cardiac cycle.

These assumptions may turn out to be erroneous in certain cases and thus result in a wrong estimate of the ESPVR.

SUMMARY OF THE DISCLOSURE

The present disclosure proposes a new method for measuring heart contractility, which avoids at least some of the above drawbacks.

To this end, according to the disclosure, a method for measuring heart muscle contractility of a patient is provided, which comprises at least the following steps:

a) an excitation step during which an elastic shear wave is generated in the patient's heart muscle by causing at least one focused ultrasound wave to be emitted into the patient's body by an array of transducers;

b) an observation step during which the propagation of the shear wave is observed in an observation field in the patient's heart muscle, this observation step comprising the following substeps:

b1) causing the array of transducers to emit into the patient's heart a succession of unfocused ultrasound compression waves, the timing of said unfocused ultrasound waves being adapted so that at least some of said unfocused ultrasound waves penetrate into the observation field while the shear wave is propagating in the observation field; and b2) causing sound signals received from said observation field to be detected in real time by said array of transducers, said sound signals comprising echoes generated by the unfocused ultrasound compression wave interacting with reflecting particles in the patient's heart muscle; and c) at least one processing step including at least a substep c2) during which:

c2) at least one movement parameter is determined in the observation field, said movement parameter characterizing movements of said reflecting particles;

d) a heart contractility estimating step in which, based on variation in the movement parameter over time, at least an end-systolic elasticity parameter is determined at at least one point of the observation field, said end-systolic elasticity parameter being function of a value taken by a shear wave propagation parameter at the end of a systole, said shear wave propagation parameter being representative of the elasticity of the heart muscle.

Thanks to these dispositions, the heart contractility may be determined precisely, quickly and non-invasively, with a limited apparatus. Further, the contractility can be determined locally, so that it is possible to establish a mapping of the contractility through at least part of the heart.

In various embodiments of the method of the disclosure, one may possibly have recourse in addition to one and/or other of the following steps (which can be used either alone or in combination):

said processing step c) further includes, before said substep c2) of determining said movement parameter, a further substep c1) in which: c1) the sound signals received successively from the observation field during substep b2) are processed in order to determine successive propagation images of the shear wave;

said shear wave propagation parameter which is calculated at the heart contractility estimating step d), is selected from shear wave speed, shear modulus, Young's modulus and shear elasticity and the inverse of local strain;

at the heart contractility computing step d), said end-systolic elasticity parameter is calculated at several points of the observation field and a map of said end-systolic elasticity parameter in the observation field is determined;

at said substep b1), said unfocused ultrasound compression waves are emitted at a rate of at least 300 shots per second;

at said heart contractility estimating step d), values of said shear wave propagation parameter are determined repeatedly at several different instants, several times per second over a measuring period covering at least one cardiac cycle, and the end-systolic elasticity parameter is determined on the basis of said values of said shear wave propagation parameter;

the end-systolic elasticity parameter is function of a maximum of said values of said shear wave propagation parameter;

said measuring period is comprised between 1 s and 180 s;

at said heart contractility estimating step d), values of said shear wave propagation parameter are determined repeatedly at a rate of at least 5 times per second;

at said heart contractility estimating step d), the end of a systole is detected by electrocardiography and the end-systolic elasticity parameter is determined at said detected end of a systole;

at said heart contractility estimating step d), values of said shear wave propagation parameter are determined repeatedly at several random instants, over a measuring period covering several cardiac cycles, and the end-systolic elasticity parameter is determined as being function of a maximum of said values of said shear wave propagation parameter;

the method further includes a diastolic elasticity estimating step e) in which a diastolic elasticity parameter is determined, said diastolic elasticity parameter being function of a value taken by said shear wave propagation parameter at a diastole;

at said diastolic elasticity estimating step e), values of said shear wave propagation parameter are determined repeatedly at several different instants, several times per second over a measuring period covering at least one cardiac cycle, and the diastolic elasticity parameter is determined on the basis of said values of said shear wave propagation parameter;

the diastolic elasticity parameter is function of a minimum of said values of said shear wave propagation parameter;

at said heart contractility estimating step d), the diastole is detected by electrocardiography and the diastolic elasticity parameter is function of a value taken by said shear wave propagation parameter at said detected diastole;

at said substep c2), said movement parameter is determined in at least one predetermined measurement zone in the observation field, by one corresponding transducer which belongs to said transducer array.

the method further includes a tracking step for tracking deformations of the heart muscle so that the measurements of shear wave propagation parameter are done at a same location within the heart muscle.

The present disclosure also discloses an apparatus for measuring heart muscle contractility of a patient, comprising an array of transducers that are controlled independently of one another by at least one electronic control system adapted:

a) to generate an elastic shear wave in the patient's heart muscle by causing at least one focused ultrasound wave to be emitted into the patient's body by said array of transducers;

b) to observe propagation of the shear wave in an observation field in the patient's heart muscle, by:

b1) causing the array of transducers to emit into the patient's heart a succession of unfocused ultrasound compression waves, the timing of said unfocused ultrasound waves being adapted so that at least some of said unfocused ultrasound waves penetrate into the observation field while the shear wave is propagating in the observation field; and b2) causing sound signals received from said observation field to be detected in real time by said array of transducers, said sound signals comprising echoes generated by the unfocused ultrasound compression waves interacting with reflecting particles in the patient's heart;

c) to process the sound signals received successively from the observation field, thereby determining therefrom at least one movement parameter in the observation field, said movement parameter characterizing movements of said reflecting particles;

d) based on variation in the movement parameter over time, to determine at least an end-systolic elasticity parameter at at least one point of the observation field, said end-systolic elasticity parameter being function of a value taken by a shear wave propagation parameter at the end of a systole, said shear wave propagation parameter being representative of the elasticity of the heart muscle.

In various embodiments of the apparatus of the invention disclosure, one may possibly have recourse in addition to one and/or other of the following arrangements (which can be used either alone or in combination):

said electronic control system is adapted to determine successive propagation images of the shear wave, and to determine therefrom said movement parameter;

said shear wave propagation parameter which is calculated by said control system, is selected from shear wave speed, shear modulus, Young's modulus, shear elasticity and the inverse of local strain;

said control system is adapted to calculate said end-systolic elasticity parameter at several points of the observation field and to determine a map of said end-systolic elasticity parameter in the observation field;

said control system is adapted to have said unfocused ultrasound compression waves emitted at a rate of at least 300 shots per second;

said control system is adapted to determine repeated values of said shear wave propagation parameter at several different instants, several times per second over a measuring period covering at least one cardiac cycle, and said central unit is adapted to determine the end-systolic elasticity parameter on the basis of said values of said shear wave propagation parameter;

said control system is adapted to determine the end-systolic elasticity parameter as a function of a maximum of said values of said shear wave propagation parameter;

said measuring period is comprised between 1 s and 180 s;

said control system is adapted to determine said shear wave propagation parameter at least 5 times in a second;

the apparatus further includes an electrocardiograph connected to said control system, said control system being adapted to detect the end of a systole through said electrocardiograph and to determine the end-systolic elasticity parameter at said detected end of a systole;

said control system is adapted to determine values of said shear wave propagation parameter repeatedly at several random instants, over a measuring period covering several cardiac cycles, and to determine said end-systolic elasticity parameter as a function of a maximum of said values of said shear wave propagation parameter;

said control system is adapted to determine a diastolic elasticity parameter, said diastolic elasticity parameter being function of a value taken by said shear wave propagation parameter at a diastole;

said control system is adapted to determine repeated values of said shear wave propagation parameter at several different instants, several times per second over a measuring period covering at least one cardiac cycle, and said central unit is adapted to determine the diastolic elasticity parameter on the basis of said values of said shear wave propagation parameter;

said control system is adapted to determine the diastolic elasticity parameter as function of a minimum of said values of said shear wave propagation parameter;

the apparatus further includes an electrocardiograph connected to said central system, said control system being adapted to detect the diastole through said electrocardiograph and to determine the diastolic elasticity parameter at said detected diastole;

the apparatus further includes an electrocardiograph connected to said control system, that triggers observation of propagation of the shear wave at a precise time of the cardiac cycle and determination the shear wave propagation parameter at said precise time of the cardiac cycle;

said control system is adapted to determine said movement parameter in at least one predetermined measurement zone in the observation field, based on data coming from one corresponding transducer which belongs to the transducer array;

the control system is adapted to track deformation of the heart muscle and to determine said shear wave propagation parameter at the same location within the heart muscle;

the contractility estimation is coupled with conventional ultrasound imaging provided in real time by the system.

BRIEF DESCRIPTION OF THE DRAWINGS

Other features and advantages of the disclosure appear from the following detailed description of one embodiment thereof, given by way of non-limiting example, and with reference to the accompanying drawings.

In the drawings:

FIG. 1 is a diagrammatic view of a shear-wave imaging device in an embodiment of the invention;

FIG. 2 is a diagram showing the shear modulus of the myocardium in the left ventricle of a patient's heart (in full line) measured through the apparatus of FIG. 1, and the blood pressure in the left ventricle (in dotted lines).

DETAILED DESCRIPTION OF THE DISCLOSURE

The apparatus 1 shown on FIG. 1 is adapted for measuring contractility in an observation field including all or part of the heart 3 of a living patient 2, more specially the heart muscle. More precisely, the apparatus 1 is used to measure contractility of the myocardium 3a of the patient's heart for instance the myocardium of the left ventricle), said myocardium being covered externally by the pericardium 3b. This measurement is carried out by:

having a mechanical shear wave propagated through the heart 3 and more particularly through the myocardium 3a;

observing the propagation of this shear wave in the heart 3 (and in particular in the myocardium 3a) through reflexion of unfocused ultrasonic compression waves on diffusing particles 3c which are reflective for the ultrasound compression waves and which are naturally contained in biological tissues (The particles 3c may be constituted by any non-uniformity in the medium 3a, and in particular, by particles of collagen);

based on the observation of the shear wave propagation, determining a propagation parameter of shear waves which is representative of elasticity of the heart 3 (and in particular of the myocardium 3a) and therefore representative of its contractility.

The structure and general way of operation of the apparatus 1 has already been described in details in document U.S. Pat. No. B2-7,252,004, and will be recalled hereafter.

The apparatus 1 may include for instance:

an ultrasound transducer array 4, for instance a linear array typically including n ultrasonic transducers $T_1$-$T_n$ juxtaposed along an axis as already known in usual echographic probes (the transducer array 4 is then adapted to perform a bidimensional (2D) imaging of the observation field, but the transducer array 4 could also be a bidimensional array adapted to perform a 3D imaging of the observation field); the number n of transducers is more than 1, for instance a few tens (e. g. 100 to 300); the transducers $T_1$-$T_n$ deliver ultrasound compression wave pulses, which pulses are of the type commonly used in echography, for example having a frequency lying in the range 0.5 MHz to 100 MHz, and preferably in the range 0.5 MHz to 15 MHz, e.g. being about 2.5 MHz;

an electronic bay 5 controlling the transducer array 4 and acquiring signals therefrom;

a microcomputer 6 for controlling the electronic bay 5 and viewing ultrasound images obtained from the electronic bay 5, said microcomputer 6 including for instance a screen 6a and a keyboard 6b or other user interfaces.

The electronic bay 5 and the microcomputer 6 will be referred herein as the control system of the apparatus 1. Such control system might be constituted of more than two devices, or by one single electronic device could fulfill all the functionalities of the electronic bay 5 and of the microcomputer 6.

The electronic bay 5 may include for instance:

n analog/digital converters 7 ($E_1$-$E_n$) individually connected to the n transducers ($T_1$-$T_n$) of the transducer array 4;

n buffer memories 8 ($M_1$-$M_n$) respectively connected to the n analog/digital converters 7;

a central processing unit 9 (CPU) communicating with the buffer memories 8 and the microcomputer 6;

a digital signal processor 11 (DSP) connected to the central processing unit 9;

a memory 10 (MEM) connected to the central processing unit 9.

Besides, in some embodiments of the invention, the central processing unit 9 (or the microcomputer 6) may be connected to an electrocardiograph 12 (ECG) which measures the electrocardiogram of the patient and transmits an electrocardiographic signal to the central processing unit 9.

The transducers $T_1$-$T_n$ are controlled independently of one another by the central processing unit 9. The transducers $T_1$-$T_n$ can thus emit selectively:

either an unfocussed ultrasound compression wave;

or else an ultrasound compression wave that is focused on one or more points of the heart 3.

The wording "unfocussed ultrasound compression wave" as understood herein means any unfocussed wave illuminating the entire observation field in the heart 3, for instance:

an ultrasound compression wave that is "plane" (i.e. a wave whose wave front is rectilinear in the X,Y plane), or any other type of unfocused wave;

a wave generated by causing random sound signals to be emitted by the various transducers $T_1$-$T_n$;

or an ultrasound compression wave that is focused on one or more points of the heart 3;

or weakly focusing waves (known as "fat" transmit focusing:ratio Focal distance/Aperture>2.5);

or diverging waves such as spherical waves;

or waves focused simultaneously on several focal points;

or more generally any kind of transmit waves that do not correspond to conventional focusing using a single focal point location and a ratio Focal distance/Aperture<2.5.

During operation of the apparatus 1, the transducer array 4 is placed in contact with the skin 2a of the patient 2, for instance on the patient's thorax.

The way of operation of the apparatus 1 is controlled by the control system, i.e. the central processing unit 9 and/or the microcomputer 6, which are programmed for this way of operation. These two devices will hereafter be called the control system of apparatus 1 (of course, the control system could be different from the particular example described herein and in particular could be constituted by one single electronic device as recalled before, or by more than two electronic devices).

To observe the propagation of the shear wave in the heart 3, the control system 6, 9 of the apparatus 1 is programmed to perform several steps in succession:

a) an excitation step during which the control system 6, 9 causes an elastic shear wave to be generated in the heart 3 by causing at least one ultrasound wave that is focused in the patient's body to be emitted by the transducer array 4 (this focussed wave may be emitted by all or part of the transducers $T_1$-$T_n$);

b) an observation step during which the propagation of the shear wave is observed simultaneously at a multitude of points of the observation field in the heart 3 (and in particular in the myocardium 3$a$), this observation step comprising the following substeps:

b1) the control system 6, 9 causes the transducer array 4 to emit into the viscoelastic medium a succession of unfocused ultrasound compression waves (these unfocussed waves may be emitted by all or part of the transducers $T_1$-$T_n$) at a rate of at least 300 shots per second, for instance at least 500 shots/s (the focusing and the timing of the focussed ultrasound wave emitted in step a), and the timing of said unfocused ultrasound waves are adapted so that at least some of said unfocused ultrasound waves reach the observation field during the propagation of the shear wave through the observation field);

b2) the control system 6, 9 causes the transducer array 4 to detect sound signals received from patient's body 2 (this detection can be carried out by all or part of the transducers of the array 4), said signals comprising echoes generated by the unfocused ultrasound compression wave interacting with the reflecting particles 3$c$ in the observation field, these echoes corresponding (directly or indirectly) to successive images of the displacement of the viscoelastic medium constituting the patient's heart and in particular the patient's myocardium 3$a$; the detected signals are recorded in real time in the buffer memories $M_1$-$M_n$;

c) at least one processing step during which:

c1) the control system 6, 9 processes the successive sound signals received from the patient's body 2 during substep b2) in order to determine successive propagation images; and c2) the control system 6, 9 determines at least one movement parameter for the viscoelastic medium constituting the patient's heart 3 (and in particular the myocardium 3$a$) at various points in the observation field.

It should be noted that the above substep c2) could be omitted: more generally, the method of the invention does not require to determine propagation images, and the control system 6, 9 may determine said movement parameter by any other means.

The focused ultrasound wave emitted during the excitation step a) may be a monochromatic wave of frequency f lying in the range 0.5 MHz to 15 MHz, for example being equal to about 2.5 MHz, which is emitted for a duration of k/f seconds, where k is an integer lying in the range 50 to 5000 (e.g. being about 500) and f is expressed in Hz. Such a wave may possibly be emitted during a succession of emission periods separated by rest periods, the emission periods following one another at a rate lying in the range 5 to 1000 emissions per second.

In a variant, the focused ultrasound wave emitted during excitation step a) is a linear combination (in particular a sum) of two monochromatic signals of respective frequencies f1 and f2 such that 20 Hz≤|f1−f2|≤1000 Hz, thus producing an amplitude modulated wave having a modulation frequency |f1−f2|.

In addition, the focused ultrasound wave emitted during excitation step a) may optionally be focused simultaneously or otherwise on a plurality of points so that the shear wave as generated presents a desired wave shape (for example it is thus possible to generate a shear wave that is plane, or on the contrary a shear wave that is focused) and illuminates desired zones in the medium 2.

During step b1), which may last for example 0.1 to 180 s, e.g. 1 to 30 s, preferably 1 to 4 s, it is possible to emit unfocused ultrasound compression waves at a rate lying in the range 500 to 10,000 shots per second, and preferably in the range 1000 to 5000 shots per second (with this rate being limited by the go-and-return travel time for the compression wave through the patient's body 2: it is necessary for all of the echoes that are generated by the compression wave to have been received by the probe 6 before a new compression wave is sent).

Each unfocused ultrasound compression wave propagates through the patient's body 2 at a propagation speed that is much higher than that of shear waves (e.g. about 1500 m/s in the human body), and interacts with the reflecting particles 3$c$, thereby generating echoes or other analogous disturbances in the signal that are known in themselves under the name "speckle noise" in the field of echography.

The speckle noise is picked up by the transducers $T_1$-$T_n$ during substep b2), after each shot of an unfocused ultrasound compression wave. The signal $s_{ij}(t)$ as picked up in this way by each transducer $T_i$ after shot No. $j$ is initially sampled at high frequency (e.g. 30 MHz to 100 MHz) and digitized (e.g. on 12 bits) in real time by the analog/digital converter $E_i$ corresponding to transducer $T_i$.

The signal $s_{ij}(t)$ as sampled and digitized in this way is then stored, likewise in real time, in [a] the buffer memory $M_i$ corresponding to the transducer $T_i$.

By way of example, each buffer memory $M[i]_j$ may present a capacity of about 128 megabytes (MB), and contains all of the signals $s_{ij}(t)$ received in succession for shots j=1 to p.

In deferred time, after all of the signals $s_{ij}(t)$ corresponding to the same propagation of a shear wave have been stored, the central processing unit 9 processes these signals (or have them processed by another circuit such a summing circuit, or the microcomputer 6 may process the signals itself) using a conventional path-forming step corresponding to substep c1).

This generates signals $S_j(x,y)$ each corresponding to the image of the observation field after shot No. $j$.

For example, it is possible to determine a signal $S_j(t)$ by the following formula:

$$S_j(t) = \sum_{i=1}^{n} \alpha_{[i]i}(x, y) \cdot s_{ij}[t(x, y) + d_{[i]i}(x, y)/V]$$

where:

$s_{ij}$ is the raw signal perceived by the transducer No. i after ultrasound compression wave shot No. j;

t(x,y) is the time taken by the ultrasound compression wave to reach the point of the observation field having coordinates (x,y), with t=0 at the beginning of shot No. j;

$d_{[i]i}(x,y)$ is the distance between the point of the observation field having coordinates (x,y) and transducer No. i, or an approximation to said distance;

V is the mean propagation speed of ultrasound compression waves in the viscoelastic medium under observation; and $\alpha_{[i]i}(x,y)$ is a weighting coefficient taking account of apodization relationships (in practice, in numerous cases, it is possible to assume that $\alpha_{[i]i}(x,y)=1$).

The above formula applies mutatis mutandis when the observation field is three-dimensional (with a two-dimensional array of transducers), with space coordinates (x,y) being replaced by (x,y,z).

After the optional path-forming step, the central processing unit 9 stores in the memory 10, the image signals $S_j(x,y)$ (or $S[j]_j(x)$ if the image would be in 1 dimension only, or $S[j]_j(x,y,z)$ in case of a 3D image), each corresponding to shot No. j. These signals may also be stored in the microcomputer 6 if the computer itself performs the image processing.

These images are then processed in deferred time in substep c2) by correlation and advantageously by cross-correlation either in pairs, or preferably with a reference image, as explained in U.S. Pat. No. B2-7,252,004.

The above-mentioned cross-correlation can be performed, for example, in the digital signal processor 11, or it may be programmed in the central processing unit 9 or in the microcomputer 6.

During this cross-correlation process, a cross-correlation function $<S_j(x,y),S_{j+1}(x,y)>$ is maximized in order to determine the displacement to which each particle 3c giving rise to an ultrasound echo has been subjected.

Examples of such cross-correlation calculations are given in U.S. Pat. No. B2-7,252,004.

This produces a set of displacement vectors $\bar{u}(\bar{r},t)$ generated by the shear waves in each position $\bar{r}$ of the heart 3 (and in particular of the myocardium 3a) under the effect of the shear wave (these displacement vectors may optionally be reduced to a single component in the example described herein).

This set of displacement vectors is stored in the memory 10 or in the microcomputer 6 and can be displayed, for example, in particular by means of the screen 4a of the computer, in the form of a slow motion picture in which the values of the displacements are illustrated by an optical parameter such as a gray level or a color level.

The propagation differences of the shear wave between zones having different characteristics in the medium 2 can thus be seen clearly.

The motion picture of shear wave propagation can also be superposed on a conventional echographic image, which can also be generated by the apparatus 1 described above.

Furthermore, it is also possible to calculate, instead of displacements, the deformations of the heart 3 (and in particular of the myocardium 3a) for each of the points in the observation field, i.e. vectors whose components are the derivatives of the displacement vectors respectively relative to the space variables (X and Y coordinates in the example described). These deformation vectors can be used like the displacement vectors for clearly viewing the propagation of the shear wave in the form of a motion picture, and they also present the advantage of eliminating displacements of the transducer array 4 relative to the patient's body 2 under observation.

From the displacement or deformation fields, the microcomputer 6 (or more generally the control system 6, 9) can advantageously then proceed with a map-making step d) during which, on the basis of the way in which the movement parameter (displacement or deformation) varies over time in the field of observation X, Y (or X, Y, Z with a two-dimensional array of transducers), it calculates at least one propagation parameter of the shear wave, either at certain points (at least 1 point) in the observation field as selected by the user acting on the microcomputer 6, or else throughout the observation field.

The propagation parameter of the shear wave that is calculated during the map-making step is selected, for example, from amongst: the shear modulus μ, or Young's modulus $E = 3\mu$, or the propagation speed $c_{[s]_s}$ of shear waves ( $$c_S = \sqrt{\frac{E}{3\rho}},$$

where ρ is the density of the tissues), or the shear elasticity μ1, as explained in more details in U.S. Pat. No. B2-7,252,004, or the inverse of local strain. Such propagation parameter is representative of the elasticity of the medium constituting the observation field, for instance the myocardium 3a.

This propagation parameter may be computed for instance by the microcomputer 6, repeatedly at several different instants, several times per second (e.g. at a rate of at least 5 times per second, e.g. at least 10 times per second) over a measuring period covering at least one cardiac cycle. Such measuring period is comprised between 0.1 and 180 s, for instance between 1 s and 30 s, preferably between 1 s and 4 s.

For instance, as shown on FIG. 2, the microcomputer 6 may compute the shear modulus μ of the myocardium 3a over time t (line 13 on FIG. 2). FIG. 2 shows that the shear modulus μ is also correlated to the pressure in the left ventricle (line 14 on FIG. 2) and thus to the cardiac cycle: the maximum value of the shear modulus corresponds to the end of a systole.

Based on the successive values of the propagation parameter, the microcomputer 6 may then determine an end-systolic elasticity parameter, which is a function of the value of the propagation parameter at the end of a systole. For instance, the end-systolic elasticity parameter may be equal to the value of the propagation parameter at the end of a systole.

In particular, the inventors of the present invention have demonstrated that the end-systolic value of the shear modulus $\mu_{es} = E_{max} \cdot V_{es}$, where $E_{max}$ is the end-systolic elastance and $V_{es}$ is the end-systolic ventricle volume. Therefore, $\mu_{es}$ is an index of the heart contractility, which is equivalent to $E_{max}$, and even better than $E_{max}$ since $\mu_{es}$ is independent of the ventricle volume. The same applies to the other propagation parameters mentioned above, which are closely related to $\mu_{es}$.

The value of the propagation parameter at the end of a systole may be determined by the microcomputer 6 as the maximum value of such propagation parameter over the measurement period.

As a variant, when the central processing unit 9 is connected to and external electrocardiograph 12, the end of a systole is detected by the electrocardiograph and the end-systolic value of the propagation parameter is determined as the value taken by said propagation parameter at said detected end of a systole.

As another variant, the values of said shear wave propagation parameter may be determined repeatedly at several random instants (possibly with a rate of less than 5 measurements per second), over a measuring period covering several cardiac cycles (for instance at least 2 or at least 3 cycles, e.g. more than 5 cycles), and the end-systolic value of the propagation parameter is then determined by the microcomputer 6 as the maximum of said values of said shear wave propagation parameter.

Of course, as mentioned above, the end-systolic elasticity parameter may be calculated at one point only or at several points of the observation field and a map of said end-systolic elasticity parameter in the observation field can then be shown on the screen 6a of the microcomputer 6.

Further, a diastolic elasticity parameter may possibly also be determined, said diastolic elasticity parameter being a function of the value taken by said shear wave propagation parameter at a diastole. For instance, the diastolic elasticity parameter may be equal to the value taken by said shear wave propagation parameter at the diastole. The diastolic value of the propagation parameter may be determined as the minimum of the values of said shear wave propagation parameter during the observation period (as in the case of the end-systolic measure, the diastolic measurement may imply either fast rate measurements at a rate of at least 5 measurements of the shear wave propagation parameter per second over at least one cardiac cycle, or random measurements, possibly a rate of less than 5 measurements of the shear wave propagation parameter per second, over more than one cardiac cycle), or, when an electrocardiograph 12 is connected to the central processing unit 9, the diastole may be detected by electrocardiography and the diastolic value of the propagation parameter is determined as the value taken by said shear wave propagation parameter at said detected diastole.

It should be noted that the method of the invention may further include a tracking step for tracking deformations of the heart muscle (due to movements of the heart) so that the measurements of shear wave propagation parameter are done at a same location within the heart muscle (for the end-systolic measurement or the diastolic measure).

Besides, the contractility estimation as described above may be coupled with conventional ultrasound imaging provided in real time by the same apparatus.

Finally, instead of computing an image of the heart muscle at substep c1) for determining the movement parameter at substep c2), it would be possible to use the method and apparatus described in document WO-A-2008/139 245 for determining locally said movement parameter in one or several predetermined measurement zone in the observation field, for each measurement zone by one corresponding transducer of the transducer array 4.

The invention claimed is:

1. A Method for measuring heart muscle contractility of a patient, comprising at least the following steps:
   a) an excitation step during which an elastic shear wave is generated in the patient's heart muscle by causing at least one focused ultrasound wave to be emitted into the patient's body by an array of transducers;
   b) an observation step during which the propagation of the shear wave is observed in an observation field in the patient's heart muscle, this observation step comprising the following substeps:
      b1) causing the array of transducers to emit into the patient's heart muscle a succession of unfocused ultrasound compression waves, the timing of said unfocused ultrasound waves being adapted so that at least some of said unfocused ultrasound waves penetrate into the observation field while the shear wave is propagating in the observation field; and
      b2) causing sound signals received from said observation field to be detected in real time by said array of transducers, said sound signals comprising echoes generated by the unfocused ultrasound compression waves interacting with reflecting particles in the patient's heart muscle; and
   c) a processing step including a substep in which at least one movement parameter is determined in the observation field, said movement parameter characterizing movements of said reflecting particles; and
   d) a heart contractility estimating step in which, based on variation in the movement parameter over time, values of said shear wave propagation parameter are determined repeatedly at several different instants, several times per second over a measuring period covering at least one cardiac cycle and at least an end-systolic elasticity parameter is determined at at least one point of the observation field on the basis of said values of said shear wave propagation parameter, said shear wave propagation parameter being representative of the elasticity of the heart muscle, a maximum of said values of said shear wave propagation parameter is determined and said end-systolic elasticity parameter is determined as a function of said maximum, said end-systolic elasticity parameter corresponding to said heart contractility.

2. The Method as claimed in claim 1, wherein said processing step further includes a further substep in which the sound signals received successively from the observation field during substep b2) are processed in order to determine successive propagation images of the shear wave before said substep in which at least one movement parameter is determined.

3. The Method as claimed in claim 1, wherein said shear wave propagation parameter which is calculated at the heart contractility estimating step d), is selected from shear wave speed, shear modulus, Young's modulus and shear elasticity and the inverse of local strain.

4. The Method as claimed in claim 1, wherein at the heart contractility computing step d), said end-systolic elasticity parameter is calculated at several points of the observation field and a map of said end-systolic elasticity parameter in the observation field is determined.

5. The Method as claimed in claim 1, wherein at said substep b1), said unfocused ultrasound compression waves are emitted at a rate of at least 300 shots per second.

6. The Method as claimed in claim 1, wherein said measuring period is comprised between 1 s and 180 s.

7. The Method as claimed in claim 1, wherein at said heart contractility estimating step d), values of said shear wave propagation parameter are determined repeatedly at a rate of at least 5 times per second.

8. The Method as claimed in claim 1, wherein at said heart contractility estimating step d), the end of a systole is detected by electrocardiography and the end-systolic elasticity parameter is determined at said detected end of a systole.

9. The Method as claimed in claim 1, wherein at said heart contractility estimating step d), values of said shear wave propagation parameter are determined repeatedly at several random instants, over a measuring period covering several cardiac cycles, and the end-systolic elasticity parameter is determined as being function of a maximum of said values of said shear wave propagation parameter.

10. The Method as claimed in claim 1, further including a diastolic elasticity estimating step e) in which a diastolic elasticity parameter is determined, said diastolic elasticity parameter being function of a value taken by said shear wave propagation parameter at a diastole.

11. The Method as claimed in claim 10, wherein at said diastolic elasticity estimating step e), values of said shear wave propagation parameter are determined repeatedly at several different instants, several times per second over a measuring period covering at least one cardiac cycle, and the diastolic elasticity parameter is determined on the basis of said values of said shear wave propagation parameter.

12. The Method as claimed in claim 11, wherein the diastolic elasticity parameter is function of a minimum of said values of said shear wave propagation parameter.

13. The Method as claimed in claim 11, wherein at said heart contractility estimating step d), the diastole is detected by electrocardiography and the diastolic elasticity parameter is function of a value taken by said shear wave propagation parameter at said detected diastole.

14. The Method as claimed in claim 1, wherein at said substep, said movement parameter is determined in at least one predetermined measurement zone in the observation field, by one corresponding transducer which belongs to said transducer array.

15. The Method according to claim 1, further including a tracking step for tracking deformations of the heart muscle so that the measurements of shear wave propagation parameter are done at a same location within the heart muscle.

* * * * *